United States Patent [19]

Carter, III

[11] Patent Number: 5,475,223
[45] Date of Patent: Dec. 12, 1995

[54] SYSTEM FOR MONITORING EXHAUST GAS COMPOSITION

[75] Inventor: Roscoe O. Carter, III, Dearborn, Mich.

[73] Assignee: Ford Motor Company, Dearborn, Mich.

[21] Appl. No.: 233,105

[22] Filed: Apr. 25, 1994

[51] Int. Cl.⁶ .......................... G01N 21/36; F01B 25/04
[52] U.S. Cl. ................... 250/339.13; 250/339.06; 250/341.6
[58] Field of Search .................. 250/339.13, 339.06, 250/341.6

[56] References Cited

U.S. PATENT DOCUMENTS

| | | | |
|---|---|---|---|
| 3,651,322 | 3/1972 | Elliott | 250/341.6 |
| 3,694,164 | 9/1972 | Guenther | 422/58 |
| 3,697,226 | 10/1972 | Hirschfeld et al. | 422/88 |
| 3,973,848 | 8/1976 | Jowett et al. | 356/51 |
| 5,060,505 | 10/1991 | Tury et al. | 73/1 G |
| 5,099,680 | 3/1992 | Fournier et al. | 73/23.31 |
| 5,184,017 | 2/1993 | Tury et al. | 250/343 |
| 5,210,702 | 5/1993 | Bishop et al. | 364/496 |

*Primary Examiner*—Constantine Hannaher
*Attorney, Agent, or Firm*—P. Abolins; R. L. May

[57] ABSTRACT

The composition of an exhaust gas stream from an internal combustion engine is analyzed using an infrared sensor detecting infrared radiation from a catalyst passing the exhaust gas. The infrared sensor provides signals indicating the presence of certain gases. These signals can be used to generate an engine control strategy to adjust the composition of the exhaust gas.

9 Claims, 1 Drawing Sheet

SYSTEM FOR MONITORING EXHAUST GAS COMPOSITION

BACKGROUND OF THE INVENTION

1. Field of the Invention

This invention relates to electronic engine controls and electronic diagnostics for an internal combustion engine.

2. Prior Art

U.S. Pat. No. 5,099,680 teaches an onboard system for analyzing exhaust gas emissions using a non-dispersive infrared gas analyzer system such as disclosed in U.S. Pat. No. 5,060,505.

Non-dispersive Infrared (IR) gas analyzers utilize an IR source to direct IR radiation though a mixture of gases contained in a sample chamber. The IR energy is passed through the mixture in the sample chamber at absorption frequencies for gases whose concentration is to be determined. The detected absorption at each frequency is indicative of the concentration of the component gas having the particular absorption band. In the particular application to automotive gas analyzers, the gases whose concentrations are of interest include HC (hydrocarbons), CO and $CO_2$. In order to measure the concentration of these gases, multiple light filters, having transmission bands at an absorption band for each component gas, are alternatingly placed between the source and detector to provide an indication for each gas. The detector output is a single, time-multiplexed signal which contains information for all component gas concentrations. This signal is conventionally demultiplexed into individual signals and applied to separate amplifier channels for each gas component.

Thus, it is known to make measurements, mostly non-dispersive infrared absorption measurements, in a traditional and well controlled fashion in order to obtain precise and accurate assessments of exhaust gas components. However, such methods require samples that are external to the vehicle, i.e., after exiting the exhaust pipe or after removal of a portion of the tail pipe flow.

It would be desirable to be able to measure the exhaust composition in a less controlled environment at the face of a catalyst coupled to the exhaust flow from an internal combustion engine. In particular, it would be desirable to make this measurement either before and/or after passage through the catalyst.

Also known are oxygen sensors coupled to the exhaust stream. However, such sensors are limited to sensing oxygen. It would be desirable to have a sensor which could sense any of a variety of species other than oxygen, i.e., carbon dioxide, carbon monoxide, oxides of nitrogen, water and hydrocarbons. This invention provides such advantages.

SUMMARY OF THE INVENTION

This invention includes a system for detecting the absorption of infrared (IR) radiation from an automotive catalyst, thereby monitoring the exhaust gas composition. The catalyst serves as a source of IR radiation for the optical absorption measurement. Radiant temperature measurements can also be made.

This invention is directed towards the issues and problems of automobile exhaust dynamics and engine control and provides better catalyst control and an on-line temperature sensor which improves engine and emissions control.

DETAILED DESCRIPTION OF THE INVENTION

Figure 1:
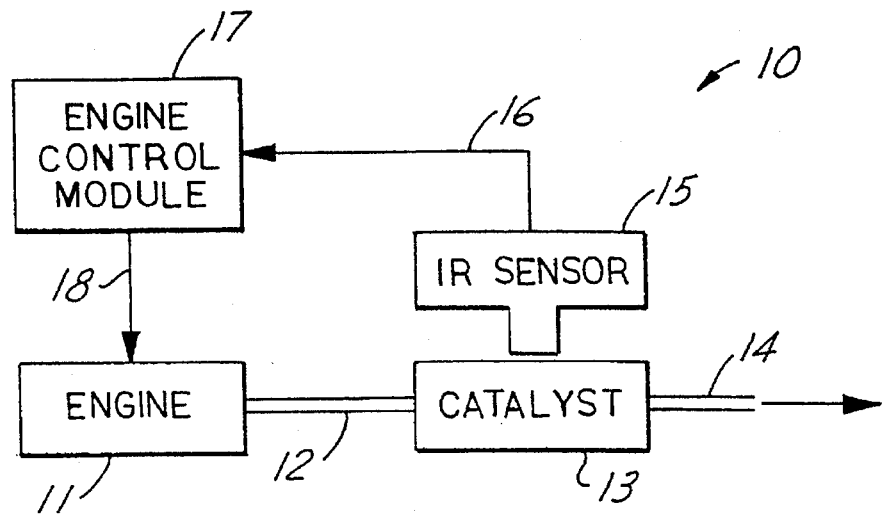
FIG. 1 is a block diagram of an engine control and diagnostic system in accordance with an embodiment of this invention.

Referring to FIG. 1, a system 10 to monitor exhaust gas composition using the catalyst as a black body radiation source includes an engine 11 which provides an exhaust gas to a pipe 12 which is coupled to a catalyst assembly 13 which in turn provides exhaust flow to a pipe 14. An IR sensor assembly 15 is coupled using an optical window to the exhaust flow upstream of catalyst assembly 13 and senses infrared radiation and temperature. A signal path 16 couples a signal from IR sensor assembly 15 to an engine control module 17. Engine control module 17 provides a control signal through a path 18 to engine 11 for operation of engine 11.

In operation, catalyst assembly 13 is used as the source of infrared radiation which is measured using IR sensor assembly 15. The IR radiation source is created after lightoff of catalyst assembly 13 at which time the surface of catalyst assembly 13 becomes hotter than the incoming gases. Such a sensor concept can be used in onboard diagnostic and control applications. By monitoring the absorption of infrared radiation at specific optical (IR) frequencies, speciation of an exhaust gas stream can be accomplished. By performing this analysis upstream of catalyst assembly 13 the performance of system 10 and engine 11 can be optimized.

IR sensor assembly 15 uses narrow pass filters so that specific infrared wave lengths can be detected. The measured magnitude of the absorption for each specific wavelength is indicative of the concentration of specific molecules or classes of molecules. Look-up tables can be used for the conversion of absorption measurements to molecule concentration. Such tables are advantageously stored in engine control module 17 and are coupled to processing control units for the control of engine 11. That is, such data can be used to established a strategy to optimize the performance of the engine 11 and/or exhaust system including catalyst assembly 13.

Figure 2:
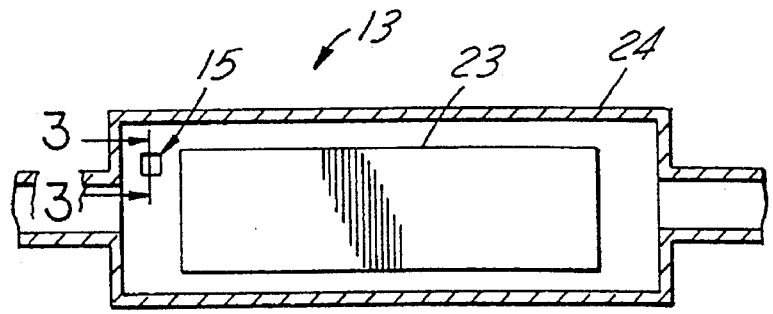
FIG. 2 is an illustrative representation of a configuration for monitoring exhaust composition using catalyst as a black body radiation source in accordance with an embodiment of this invention.

Referring to FIG. 2, catalyst assembly 13 includes a catalyst 23 with a surface area acting as an immediate source for infrared radiation. Infrared sensor assembly 15 receives radiation from catalyst 23 through an opening 19 in a catalyst containment can 24.

Figure 3:
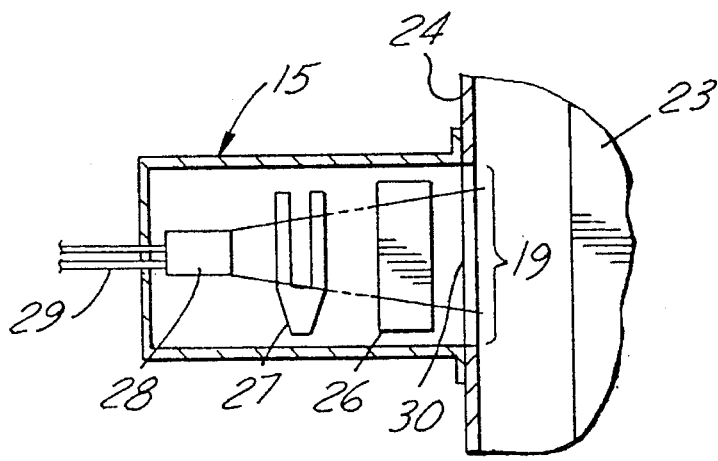
FIG. 3 is an illustration showing the configuration of an infrared sensor device and its internal components in accordance with an embodiment of this invention.

Referring to FIG. 3, sensor assembly 15 is mounted to opening 19, with a window 30 flush to the surface of containment can 24. Radiation entering sensor assembly 15 from catalyst 23 passes through window 30, filters 26, a tuning fork 27 and then strikes an IR detector 28. An output signal from detector 28 is carried by output leads 29.

Radiation from catalyst 23 indicative of the current operating temperature interacts with the gases present in the chamber. The gases will interact to absorb the radiation in a manner related to the corresponding molecular structures of the component species and the temperature of the gases relative to the temperature of the catalyst's radiation-emitting surface. Radiation measurements can be accomplished by infrared detector 28 such as pyrometers arranged behind narrow band pass optical filters 26 such as interference filters, holographic filters or tunable filters. Advantageously, the measurement process uses some mode of producing modulation of the intensity of the radiation.

Optical filters 26 are used and selected to limit the radiation incident on detector 28 to the region of the infrared spectrum where one of the specific gas species to be measured exhibits molecular transitions. By measurements of the infrared spectrum an indication of the concentration of the species measured can be made. An optical measurement for each species to be quantified must be made. However, only one reference is required when all measurements are made over a time frame where the system in general is operating in a stable fashion. The modulation, provided by tuning fork 27 in this embodiment, provides a method to reduce detector drift, and provides a means to discriminate against other sources of noise by recording only the signal that has the modulation signature. Modulation may also be accomplished by switching rapidly between several filters settings and making several measurements with one detector element.

By making the measurements in the catalyst containment can upstream and downstream of the catalyst, a measure of catalyst efficiency can be made in situ both for long term efficiency assessment and for improved dynamic engine control.

Various variations and modifications will no doubt occur to those skilled in the art. Such variations and modifications are considered within the scope of the appended claims.

What is claimed:

1. A method of analyzing the composition of an exhaust gas stream from an internal combustion engine passing through a catalyst, including the steps of:

using the catalyst as a source of infrared radiation with which to make species or molecular class quantity measurements;

positioning an infrared sensor in optical communication with the catalyst; and, generating an electrical signal in response to infrared radiation sensed by the sensor and using the generated electrical signal to control engine operation.

2. A method as recited in claim 1 wherein the step of generating the electrical signal includes the steps of:

using narrow pass filters in the path of the infrared radiation whereby specific infrared wave lengths can be detected; and using look-up tables for processing such electrical signal to determine the concentration of specific molecules and classes of molecules.

3. A method as recited in claim 2 further including the step of modulating the infrared radiation from the catalyst.

4. A method as recited in claim 3 wherein the step of modulating the infrared radiation includes positioning a tuning fork in the path of the radiation.

5. A method of controlling the operation of an internal combustion engine having an exhaust path with a catalyst, using an engine control module, including the steps of:

positioning an infrared sensor adjacent the catalyst;

generating an electrical signal in response to the infrared radiation sensed by the sensor;

applying the electrical signal to the engine control module and using look-up tables to convert measurements of infrared frequencies with respect to spectra absorption bands to concentration of specific molecules and classes of molecules;

generating an engine control strategy in response to such measurements of infrared frequencies; and using the engine control strategy to control the engine and improve engine operation so as to adjust the exhaust gas composition as desired.

6. An apparatus for analyzing the composition of an exhaust gas stream from an internal combustion engine passing through a catalyst including:

an infrared window for providing optical communication to the catalyst so that infrared radiation can pass from the catalyst through the exhaust gas and then out said window; and an infrared sensor adjacent said window for receiving the infrared energy passing through the window and generating an electrical signal.

7. An apparatus as recited in claim 6 further comprising:

a plurality of filters positioned between said window and said infrared sensor; and means for modulation of the infrared radiation between said sensor and said window.

8. An apparatus as recited in claim 7 wherein said means for modulation includes a tuning fork.

9. An apparatus as recited in claim 7 further comprising:

an electronic engine control module coupled to said infrared sensor for processing the electrical signal using stored look-up tables relating the electrical signal to specific molecules and classes of molecules.

* * * * *